United States Patent [19]
Gelfand

[11] Patent Number: 5,837,688
[45] Date of Patent: Nov. 17, 1998

[54] USE OF THROMBOLYTIC REAGENTS FOR PREVENTION OF VASCULAR DISEASE

[76] Inventor: Mathew I. Gelfand, 245 Fairway Rd., Lido Beach, N.Y. 11561

[21] Appl. No.: 758,615

[22] Filed: Nov. 27, 1996

[51] Int. Cl.[6] .................................................. A61K 38/00
[52] U.S. Cl. .................................................. 514/21; 514/2
[58] Field of Search ............................................. 514/2, 21

[56] References Cited

U.S. PATENT DOCUMENTS

| | | | |
|---|---|---|---|
| 4,853,330 | 8/1989 | Goeddel et al. | 435/226 |
| 5,156,969 | 10/1992 | Gill et al. | 435/240.2 |
| 5,262,170 | 11/1993 | Anderson et al. | 424/94.64 |
| 5,288,503 | 2/1994 | Wood et al. | 424/497 |
| 5,385,732 | 1/1995 | Anderson et al. | 424/94.64 |
| 5,426,097 | 6/1995 | Stern et al. | 514/12 |

FOREIGN PATENT DOCUMENTS

| | | |
|---|---|---|
| 297860 B1 | 4/1989 | European Pat. Off. . |
| 0 199 574 | 10/1991 | European Pat. Off. . |
| 0 297 860 | 9/1993 | European Pat. Off. . |

OTHER PUBLICATIONS

Bick et al., "Thrombolytic Therapy and Its Uses", Lab .Med. 26:330–337, May 1995.

Shabahang et al., 1994, "The Clinical Impact of Risk Factor and Prophylaxis on Pulmonary Embolism", J. Vasc. Dis. 45:749–754.

Vipond et al., 1994, "Experimental Adhesion Prophylaxis with Recombinant Tissue Ploasminogen Activator", Ann. R. Coll. Surg. Engl. 76:412–415.

Mohr et al., 1988, "Recent Advances in the Management of Venous Thromboembolism", Mayo Clin. Proc. 63:281–290.

Pannekoek et al., 1988, "Mutants of Human Tissue–Type Plasminogen Activator (t–PA): Structural Aspects and Functional Properties", Fibrinolysis 2:123–132.

Rose et al., 1988, "Plasminogen Activators", Ann. Rep. Med. Chem. 23:111–119.

Harris, 1987, "Second–Generation Plasminogen Activators", Prot. Eng. 1:449–458.

Fass and Toole, 1985, "Genetic Engineering and Coagulation Factors", Clin. Haem. 14:547–570.

*Primary Examiner*—Marianne M. Cintins
*Assistant Examiner*—Dwayne C. Jones
*Attorney, Agent, or Firm*—Pennie & Edmonds LLP

[57] ABSTRACT

The present invention relates to the administration of thrombolytic reagents such as tissue plasminogen activator (t-PA), streptokinase and/or urokinase, over prolonged periods of time for prevention of vascular disease such as cerebral vascular thrombosis, pulmonary embolism, deep venous thrombus, acute myocardial infarction and fresh or aged arterial thrombi. The invention relates generally to delivery systems that provide for sustained release of thrombolytic reagents such as tissue plasminogen activator (t-PA), streptokinase and/or urokinase, over prolonged periods of time. The thrombolytic reagents may be administered, for example, transdermally, topically, intranasally or orally.

17 Claims, No Drawings

USE OF THROMBOLYTIC REAGENTS FOR PREVENTION OF VASCULAR DISEASE

INTRODUCTION

The present invention relates to the administration of thrombolytic reagents such as tissue plasminogen activator (t-PA), streptokinase and/or urokinase, over prolonged periods of time for prevention of vascular disease such as cerebral vascular thrombosis, pulmonary embolism, deep venous thrombus, acute myocardial infarction and fresh or aged arterial thrombi. The invention relates generally to delivery systems that provide for sustained release of thrombolytic reagents such as tissue plasminogen activator (t-PA), streptokinase and/or urokinase, over prolonged periods of time. The thrombolytic reagents may be administered, for example, transdermally, topically, intranasally or orally.

BACKGROUND OF THE INVENTION

TISSUE PLASMINOGEN ACTIVATOR

Thrombolytic drugs act on the endogenous fibrinolytic system by converting plasminogen to the potent proteolytic enzyme plasmin. Plasmin in turn degrades fibrin clots and other plasma proteins. A number of thrombolytic drugs, including urokinase, streptokinase and t-PA, are currently used to treat acute vascular disease.

Tissue plasminogen activator (t-PA) activates plasminogen to generate the proteinase plasmin which plays an important role in the degradation of fibrin. t-PA has been a particularly important pharmaceutical agent for use in treatment of vascular diseases due to its ability to dissolve blood clots in vivo. t-PA was originally identified and purified from natural sources. Through the use of recombinant DNA techniques, DNA clones encoding the t-PA molecule have recently been identified and characterized leading to a determination of the DNA sequence and deduced amino acid sequence of t-PA (U.S. Pat. No. 4,853,330).

Several variants of t-PA have also been developed that address some of the disadvantages associated with the use of t-PA. These disadvantages include the short half life and fast clearance rate of t-PA. Such variants include those described in EPO Patent Publication No. 199,574, that have amino acid substitutions at the proteolytic cleavage sites at amino acid positions 275, 276 and 277. These forms are referred to as protease-resistant one-chain t-PA variants in that, unlike natural t-PA, they exist in either one chain or two chain form, are resistant to proteolytic cleavage and exist in one-chain form. Such variants are thought to be superior to natural t-PA for pharmaceutical uses in that they are more stable. In addition, a variety of glycosylation mutants exist at positions 117, 119, 184–186 and 448–450 which exhibit higher specific activity than natural t-PA.

A general review of plasminogen activators and derivatives thereof can be found in Harris (1987, Protein Engineering 1:449–458); Pannekock et al. (1988, Fibrinolysis 2:123–132); and Ross et al. (1988, Annual Reports in Medicinal Chemistry, Vol. 23, Chapter 12), each of which is incorporated by reference herein.

VASCULAR DISEASE

Thrombosis and its complications are considered the most frequent causes of morbidity and death in the adult population. Pulmonary embolism is estimated to be the third most common cause of death in the United States (Mohr et al., 1988, Mayo Clin. Proc. 63:281–290). At present, anticoagulation is the basic approach to treatment of thromboembolic disorders (Bick, R. et al., 1995, Laboratory Medicine 26:330–337; Shabahang, M. et al., 1994, Angiology 45:749–754). Pharmaceutical preparations containing thrombolytic reagents such as t-PA, urokinase and streptokinase are currently used for treatment of acute vascular disease.

Short term administration of pharmaceutical preparations containing thrombolytic reagents, such as t-PA, urokinase or streptokinase, are currently used to treat patients suffering from cardiovascular diseases or conditions. For example, t-PA is parentally administered to patients as a means for treatment of deep vein thrombosis or peripheral vascular disease. t-PA is also used in connection with emergency medical care facilities for treatment of arterial embolisms which include pulmonary and extremity embolisms and infarction.

The deposition of fibrin in the peritoneal cavity may lead to fibrous adhesion formation which are the most common cause of small bowel obstruction in developed countries (Vipond et al., 1994, Ann. R. Coll. Surg. Engl. 76:412–415; EP 0297860 B1). t-PA has also been used successfully to prevent fibrin deposition or adhesion formation in the peritoneal cavity following surgery, infection, trauma or inflammation.

SUMMARY OF THE INVENTION

The present invention relates to methods for preventing vascular disease by the chronic administration of low doses of thrombolytic reagents such as tissue plasminogen activator (t-PA), streptokinase and/or urokinase, over prolonged periods of time. The present invention also relates to delivery systems that can be used in the methods of the invention. For example, systems that provide for sustained release of thrombolytic reagents, such as t-PA, over prolonged periods of time can be used. In general, the total daily dose range of t-PA should be sufficient to achieve serum concentrations of between about 1 and 50 mgs. For example, between about 1 and 50 mgs of a daily parenteral dose may be administered, most preferably a daily dose range should be between 10 and 30 mgs of t-PA. Therefore, an object of the invention is to provide dose-controlling applicators for thrombolytic compositions such as t-PA.

The present invention may be used therapeutically as a prophylactic means for inhibiting the development of vascular diseases such as pulmonary embolus, deep venous thrombus, acute myocardial infarction and fresh or aged arterial thrombi. The invention is of particular use for treatment of individuals at high risk for vascular disease, such as, diabetics, hypertensive or hyperlipidemia patients, smokers or those individuals with a family history of vascular disease.

The present invention encompasses a number of preferred embodiments. In the first, the thrombolytic reagent is contained in a dermal patch which may be used to provide sustained release of tissue plasminogen activator into a patient's bloodstream over prolonged periods of time. In another embodiment of the invention the thrombolytic reagent may be combined with slow release gel formulations which may be applied topically to the patient. In yet another embodiment of the invention the thrombolytic reagent may be added to a biocompatible matrix material which may be implanted into the body of the patient for slow sustained release of the reagent. The thrombolytic reagent may also be administered orally or intranasally through the use of nasal sprays containing the reagent.

DETAILED DESCRIPTION OF THE INVENTION

Thrombosis and its complications are considered the most frequent causes of morbidity and death in the adult population. The present invention involves a prophylactic method for inhibiting the development of vascular disease such as pulmonary embolus, deep venous thrombus and acute myocardial infarction and cerebral vascular thrombus. The invention relates to the chronic administration of low doses of thrombolytic reagents to prevent vascular disease. The thrombolytic reagents may be administered daily, weekly, monthly or yearly depending on the type of delivery system utilized. The desired goal of any such delivery systems is a constant long term delivery of thrombolytic reagents. Such thrombolytic reagents include, for example, t-PA, streptokinase and urokinase, etc.

The invention is of particular use for treatment of individuals at high risk for vascular disease, such as, diabetics, hypertensive or hyperlipidemia patients, smokers or those individuals with a family history of vascular disease. In such patients, the delivery of a continuous sustained release of thrombolytic reagents, such as t-PA, streptokinase or urokinase, may prevent the development of vascular disease.

Thus, the present invention relates to the chronic administration of low doses of thrombolytic reagents such as tissue plasminogen activator, streptokinase and/or urokinase over prolonged periods of time for prevention of vascular disease. The invention further relates to delivery systems that provide for long-term sustained release of thrombolytic reagents, such as t-PA, in the blood, which is effective as a means for preventing the development of vascular disease. The object of the invention is the prevention or dissolving of clots as they form in the vascular system of the treated patient. In accordance with the present invention, the object can be achieved through the use of t-PA preparations designed for sustained release of t-PA into the bloodstream of a patient over prolonged periods of time.

THROMBOLYTIC REAGENTS

The thrombolytic reagents to be used in the practice of the invention, herein defined as any reagents which have fibrinolytic activity, may be derived from a variety of different sources. For example, the t-PA may be produced in large quantities using recombinant DNA techniques well known to those skilled in the art such as those disclosed in U.S. Pat. No. 4,853,330 which is incorporated herein by reference. Alternatively, the t-PA may be obtained from a number of commercially available sources such as Activase© supplied by Genentech, Inc.

When using t-PA, it is within the scope of the invention that variants of naturally occurring t-PA may also be used in the practice of the invention. In preferred embodiments, such variants of t-PA may have an increased half life or a slower rate of clearance from the body. For example, variants having amino acid substitutions at the proteolytic cleavage sites at position 275, 276 and 277 which render t-PA preparations more stable may be used. Glycosylation mutants at amino acids 117–119, 184–186 and 448–45 exhibit a higher specific activity and such variant may also be used in the practice of the invention. t-PA can also be modified to delete amino acids 51–87 which results in a variant having a slower clearance from plasma. These variants represent only a subset of the known variants of t-PA which may be used in the presently claimed delivery systems.

It is also within the scope of the present invention that thrombolytic reagents other than t-PA may be used in the practice of the invention. Such agents include urokinase and streptokinase both of which may be obtained from commercial sources (Urokinase, Abbott Laboratories; Streptokinase, Pharmacia Adria).

METHOD OF PREVENTING VASCULAR DISEASE

The present invention relates to methods of preventing vascular disease by chronic administration of low doses of thrombolytic reagents. The present invention may be used as a prophylactic means for inhibiting the development of vascular diseases such as cerebral vascular thrombosis, pulmonary embolus, deep venus thrombus and acute myocardial infarction. The invention is of particular use for treatment of individuals at high risk for vascular diseases.

Pharmaceutical compositions suitable for use in the present invention include compositions wherein the thrombolytic ingredients are contained in an effective amount to achieve its intended purpose. More specifically, a therapeutically effective amount means an amount effective to prevent development of vascular disease in the subject being treated. A therapeutically effective dose refers to that amount of the compound that results in plasma levels of the thrombolytic reagent which are sufficient to maintain the beneficial modulating effects. Determination of the effective amounts is well within the capability of those skilled in the art.

The effective dose may be determined using a variety of different assays. For example, assays may be utilized to determine levels of fibrinogen or fibrin split products in the blood of treated patients. In such instances, the effective dose of the thrombolytic reagent is that amount required to sustain normal levels of fibrinogen or fibrin split products in the body of the patient. Such doses may be determined by measuring for levels of fibrinogen (assay for measuring levels of fibrinogen is available from M.L.A.,Inc.) or fibrin split products (Thrombo-Wellco Test;MUREX, Inc.) in the blood of treated patients. A therapeutically effective dose refers to that amount of thrombolytic reagent sufficient to maintain normal circulating blood levels of about 2–4 mg/ml of fibrinogen, or, less than 10 mg/ml of fibrin split products.

The amount of composition administered will, of course, be dependent on the subject being treated, on the subject's weight, the severity of the affliction, the manner of administration and the judgment of the prescribing physician. It should be noted that the attending physician would know how to and when to terminate, interrupt or adjust therapy to lower dosage due to toxicity. Conversely, the attending physician would also know to adjust treatment to higher levels if the clinical response is not adequate (precluding toxicity).

In administering thrombolytic reagents to the patient, it is particularly important to monitor the patient for excessive bleeding or tendencies to bleed. A variety of different diagnostic tests, which are well known to those skilled in the art may be used to access the patients susceptibility to bleeding due to administration of the thrombolytic reagents. Such assays include a complete blood count (CBC), or a determination of prothrombin or partial prothrombin time.

The magnitude of a prophylactic dose of the t-PA in the management of vascular disease will vary with the patient to be treated and the route of administration. Again, it should be noted that the clinician or physician would know when to interrupt and/or adjust the treatment dose due to toxicity. The dose, and perhaps the dosage frequency, will also vary according to the age, body weight, and response of the individual patient.

In general, the total daily dose range of t-PA should be sufficient to achieve serum concentration levels ranging between 1 and 50 mgs. For example, between about 1 and 50 mgs of a daily parenteral dose may be administered, while most preferably a daily dose range should be between about 10 and 30 mgs of a parenteral dose of t-PA. For smaller patients (less than 65 kg), a dose of 0.1–0.5 mg/kg may be administered daily. It is further recommended that infants, children, and patients over 65 years, and those with impaired renal, or hepatic function, initially receive low doses, and that they be titrated based on individual clinical response(s) and blood level(s). It may be necessary to use dosages outside these ranges in some cases as will be apparent to those of ordinary skill in the art.

THROMBOLYTIC DRUG DELIVERY SYSTEMS

A variety of drug delivery systems may be used to deliver the thrombolytic reagents, such as t-PA into the bloodstream of the patient. For example, the t-PA can be administered to a human patient in pharmaceutical compositions where it is mixed with suitable carriers or excipient(s) at doses therapeutically effective to prevent a variety of vascular disorders. Suitable routes of administration may, for example, include transdermal, topical, oral, intranasal and the like. Dosage forms include but are not limited to aerosol dispersions, creams, patches and the like.

For purposes of clarity, the following discussion describes delivery systems for t-PA. However, the delivery systems are not so limited. It is understood that the delivery systems described below may also be utilized for delivery of other thrombolytic reagents such as urokinase and streptokinase. Techniques for formulation and administration of the thrombolytic reagents of the instant application may be found in "Remington's Pharmaceutical Sciences," Mack Publishing Co., Easton, Pa., latest edition.

Pharmaceutical compositions for use in accordance with the present invention thus may be formulated in conventional manner using one or more physiologically acceptable carriers comprising excipients and auxiliaries which facilitate processing of the t-PA into preparations which can be used pharmaceutically. Proper formulation is dependent upon the route of administration chosen. Suitable routes of administration may, for example, include transdermal, topical, oral, intranasal and the like. Dosage forms include but are not limited to aerosol dispersions, creams, patches and the like.

The formulations of the present invention normally will consist of t-PA with a carrier, or diluted by a carrier. Some examples of the diluents or carriers which may be employed in the pharmaceutical compositions of the present invention are lactose, dextrose, sucrose, sorbitol, mannitol, propylene glycol, liquid paraffin, white soft paraffin, kaolin, microcrystalline cellulose, calcium silicate, silica polyvinylpyrrolidone, cetostearyl alcohol, starch, gum acacia, calcium phosphate, cocoa butter, oil of theobroma, arachis oil, alginates, tragacanth, gelatin, syrup B.P., methyl cellulose, polyoxyethylene sorbitan monolaurate, ethyl lactate and propylhydroxybenzoate, sorbitan trioleate, sorbitan sesquioleate and oleyl alcohol.

Because of the short shelf life of t-PA in solution, formulations of t-PA in aqueous solutions, gels, etc. are stored under refrigeration to preserve the activity of the t-PA. Lyophilized preparations of t-PA may be stored at room temperature and protected from excessive exposure to light without loss of activity.

A variety of different drug delivery systems may be used to deliver t-PA into the bloodstream of the patient. In one particular embodiment of the invention a dermal patch may be used for sustained delivery of t-PA into the body. These membrane systems are designed to deliver controlled doses of drugs through the skin into the bloodstream.

TRANSDERMAL DELIVERY SYSTEM

Transdermal delivery of t-PA can be designed so that the rate of delivery of the t-PA closely follows the rate of clearance of the t-PA from the patient's body, thus keeping constant levels of the t-PA in the blood, thereby reducing t-PA waste and overdosing. The use of such a drug delivery system also provides a comfortable, convenient non-invasive method for unattended delivery of t-PA over a prolonged time period.

The transdermal patches to be used in the practice of the invention may be obtained from any of a variety of commercial sources. Most patches consists of a reservoir of drug material located behind a rate controlling membrane. The patch is impregnated with the t-PA and placed on the skin of the patient which allows the drug to penetrate readily into the body. In the practice of the invention the transdermal patch will be periodically replaced as the t-PA becomes depleted.

The transdermal patch is prepared to contain a solution of t-PA. The t-PA is dispersed in the solution, suspension or gel in a dissolved or undissolved state. The drug reservoir of the patch containing a solution, suspension or gel of t-PA also includes permeation enhancers which increase the skin penetration of the t-PA. Such permeation enhancers include those described in U.S. Pat. No. 4,573,966, which is incorporated by reference herein. Permeation enhancers may include plasticizer type enhancers such as lower alky and alkoxy esters of pharmaceutically acceptable fatty acids, fatty acid esters, fatty alcohols and similar hydrophobic compounds that are capable of increasing the permeability of drugs to the skin. In addition, solvent type enhancers may be used to increase the delivery of drugs through the skin. Such enhancers generally refer to relatively hydrophilic compounds having molecular weights of less than 200. More preferably, solvent type enhancers have a molecular weight of less than 150. They are also generally greater than 2 wt % soluble in water, and are preferably greater than 10 wt % soluble in water. Typically, solvent type enhancers include pharmaceutically acceptable lower alkyl alcohol, aryl alcohol, or polyol, for example, ethanol, propanol, butanol, benzyl alcohol, glycerin, or propylene glycol. as well as diluents, such as water or other additives. The solution of t-PA may be formulated to include vascular permeability factors (VPFs), as described in U.S. Pat. No. 5,503,843, which cause a rapid and reversible increase in blood vessel permeability. Such VPF may be added to the t-PA solution to facilitate the uptake of t-PA into the blood vessels of the skin. In addition, gelling agents may be added to increase the viscosity of the solution as is described in U.S. Pat. No. 5,503,843. The t-PA may also include diluents, stabilizers, biocides, antioxidants, anti-irritants and the like.

Because of the instability of t-PA in solution, it is desirable to design transdermal patches that can be stored at room temperature. Such a dermal patch may be designed, for example, with two compartments separated by a breakable barrier; one compartment contains lyophilized t-PA and the other compartment contains a solution or carrier, such as those described above, into which the t-PA is dissolved. Prior to the use of the patch, the barrier is broken, mixing the contents of both compartments thereby forming a drug reservoir containing a solution of t-PA. Alternatively, a transdermal patch may be designed with a single breakable compartment containing lyophilized t-PA, enclosed within the liquid carrier. Prior to use of the patch, the single compartment barrier is broken releasing the lyophilized t-PA into the carrier solution. The patch is then placed in contact with the skin in such a way that the drug reservoir containing the t-PA solution is in contact with the skin.

INTRANASAL DELIVERY SYSTEM

In yet another embodiment of the invention, the t-PA may be administered intranasally. The large blood supply carried in the capillaries of the nose allow drugs to enter the bloodstream quickly. For administration by inhalation, t-PA are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

In addition, the inhalers may be formulated to include vascular permeability factors (VPFs) which cause an increase in blood vessel permeability thereby facilitating the uptake of t-PA into the blood vessels of the nose.

IMPLANTABLE DELIVERY SYSTEMS

In addition to the formulations described above, the t-PA may also be formulated as a slow release preparations that may be administered by implantation (for example subcutaneously or intramuscularly) or by intramuscular injection. Thus, for example, the t-PA may be formulated with suitable biocompatible matrix materials. The compounds may be delivered using a sustained-release system, such as slow release gel formations containing the t-PA. Various slow release gel formations have been established and are well known by those skilled in the art. Sustained-release capsules may, depending on their chemical nature, release the t-PA for prolonged periods of time.

ORAL FORMULATIONS

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic aced or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures.

The t-PA is preferably formulated for oral administration with enteric coatings which protect the t-PA from enzymatic degradation in the stomach and promotes uptake by the intestinal tract. Such formulations are designed for slow release of t-PA through the intestinal wall and into the bloodstream of the patient. For example, the drug capsule containing t-PA may be coated with an enteric film which is sufficiently insoluble at a pH below 7 as to be capable of protecting the capsule and its contents from the digestive enzymes until the capsule reaches a region below the upper part of the intestine. Such film compositions include mixtures of anionic acrylic copolymers derived from at least on monomer selected from acrylic and methacrylic acids and methylacrylates. Such copolymers are commercially available under the trade name "Eudragit"(TM). Such enteric coatings are well known to those skilled in the art, and include those described in U.S. Pat. No. 4910021 and U.S. Pat. No. 5350741, each of which is incorporated by reference herein. Dyestuffs or pigments may also be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in a mixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in a conventional manner.

PARENTERAL FORMULATIONS

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulator agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

PACKAGING

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition. Suitable conditions indicated on the label may include treatment of patients at risk for development of vascular diseases, or alternatively treatment of patients suffering from vascular diseases such as cerebral vascular thrombosis, pulmonary embolism, deep venous thrombos, acute myocardial infarction and fresh or aged arterial thrombi.

EXAMPLE

TRANSDERMAL ADMINISTRATION OF THROMBOLYTIC REAGENTS

The following example describes the administration of the thrombolytic reagent t-PA utilizing a transdermal patch delivery system. The use of transdermal patches for the delivery of drugs through the skin is well known. Methods for the use of transdermal patches for delivery of drugs is described, for example, in the following United States patents, U.S Ser. Nos. 5,498,417, 5,503,844 and 5,503,843, each of which is incorporated by reference herein.

The following example illustrates the invention. It is not intended to limit the scope of the invention.

The t-PA (Activase, supplied by GENENTECH, Inc.) to be used in this example is supplied in 50 mg vials. The vials should be reconstituted in either sterile water or a pharmaceutical composition compatible with use in a transdermal patch.

The transdermal patch is prepared to contain a solution of t-PA. The t-PA is dispersed in the solution, suspension or gel in a dissolved or undissolved state. The drug reservoir of the patch containing a solution, suspension or gel of t-PA also includes permeation enhancers which increase the skin penetration of the t-PA. Such permeation enhancers include those described in U.S. Pat. No. 4,573,966, which is incorporated by reference herein. Permeation enhancers may include plasticizer type enhancers such as lower alky and alkoxy esters of pharmaceutically acceptable fatty acids, fatty acid esters, fatty alcohols and similar hydrophobic compounds that are capable of increasing the permeability of drugs to the skin. In addition, solvent type enhancers may be used to increase the delivery of drugs through the skin. Such enhancers generally refer to relatively hydrophilic compounds having molecular weights of less than 200. More preferably, solvent type enhancers have a molecular weight of less than 150. They are also generally greater than 2 wt % soluble in water, and are preferably greater than 10 wt % soluble in water. Typically, solvent type enhancers include pharmaceutically acceptable lower alkyl alcohol, aryl alcohol, or polyol, for example, ethanol, propanol, butanol, benzyl alcohol, glycerin, or propylene glycol. as well as diluents, such as water or other additives. The solution of t-PA may be formulated to include vascular permeability factors (VPFs), as described in U.S. Pat. No. 5503843, which cause a rapid and reversible increase in blood vessel permeability. Such VPF may be added to the t-PA solution to facilitate the uptake of t-PA into the blood vessels of the skin.

The amount of t-PA contained in the patch is that amount necessary to deliver a daily dose of between 1–50 mg of t-PA. The treated patient's blood is monitored to determine the levels of circulating fibrinogen and/or fibrin split products. The amount of t-PA contained in the patch is adjusted so as to maintain blood levels of about 2–4 mg/ml of fibrinogen and 10 mg/ml of fibrin split products. In addition, the treated patient is monitored to prevent excessive bleeding which can result from treatment with thrombolytic reagents.

Once the transdermal patch has been prepared to contain an appropriate dose of t-PA, in a suitable solution, the patients skin is overlaid with the transdermal patch. The patch is placed in contact with the skin in such a way that the side of the patch containing the t-PA solution side is in contact with the patient's skin.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the claims.

What is claimed:

1. A method for prevention of thrombotic vascular disease in a mammal, comprising the chronic administration to a patient in need thereof of an effective dose of a thrombolytic reagent to a mammal.

2. The method of claim 1 wherein the thrombolytic reagent is human tissue plasminogen activator.

3. The method of claim 1 wherein the thrombolytic reagent is streptokinase.

4. The method of claim 1 wherein the thrombolytic reagent is urokinase.

5. The method of claim 1 wherein the thrombolytic reagent is delivered in a transdermal patch.

6. The method of claim 5 wherein the thrombolytic reagent is selected from the group consisting of human tissue plasminogen activator, streptokinase and urokinase.

7. The method of claim 2 wherein the human tissue plasminogen activator is recombinant human tissue plasminogen activator.

8. The method of claim 1 wherein the thrombolytic reagent is delivered internasally.

9. The method of claim 8 wherein the thrombolytic reagent is selected from the group consisting of human tissue plasminogen activator, streptokinase and urokinase.

10. The method of claim 1 wherein the thrombolytic reagent is delivered topically in a topical cream.

11. The method of claim 10 wherein the thrombolytic reagent is selected from the group consisting of human tissue plasminogen activator, streptokinase and urokinase.

12. The method of claim 1 wherein the thrombolytic reagent is delivered orally.

13. The method of claim 12 wherein the thrombolytic reagent is selected from the group consisting of human tissue plasminogen activator, streptokinase and urokinase.

14. The method of claim 1 wherein the dose of the thrombolytic reagent is that dose sufficient to maintain circulating blood levels of 2–4 mg/ml of fibrinogen or less than 10 mg/ml of fibrin split products.

15. The method of claim 1 wherein the dose of the thrombolytic reagent is that dose sufficient to maintain circulating blood levels of less than 10 mg/ml of fibrin split products.

16. The method of claim 2 wherein the daily dose of t-PA is between 1–50 mg.

17. The method of claim 2 wherein the daily dose of t-PA is between 10–30 mg.

* * * * *